United States Patent [19]

Tresco et al.

[11] Patent Number: 5,453,368
[45] Date of Patent: Sep. 26, 1995

[54] METHOD OF ENCAPSULATING BIOLOGICAL SUBSTANCES IN MICROSPHERES

[75] Inventors: Patrick A. Tresco, Salt Lake City, Utah; John F. Mills, Wakefield, R.I.

[73] Assignee: Brown University Research Foundation, Providence, R.I.

[21] Appl. No.: 113,778

[22] Filed: Aug. 27, 1993

[51] Int. Cl.$^6$ .......................... B01J 13/12; C12N 11/04; C12N 11/08; C12N 11/12
[52] U.S. Cl. ............... 435/182; 264/4; 264/4.3; 264/4.6; 264/4.7; 424/93.1; 424/424; 424/425; 424/493; 424/494; 424/497; 425/5; 435/180; 435/240.22; 514/866; 514/885; 514/962; 514/963
[58] Field of Search ................... 264/4.3, 4.6, 4; 435/178, 182; 424/424, 425, 493, 494, 497, 93.1; 514/866, 885, 962; 425/5; 935/54

[56] References Cited

U.S. PATENT DOCUMENTS

| | | | |
|---|---|---|---|
| 3,523,906 | 8/1970 | Vrancken et al. | 264/4.6 |
| 3,639,306 | 2/1972 | Sternberg et al. | 424/497 |
| 3,697,286 | 10/1972 | Grün | 427/212 X |
| 4,352,883 | 10/1982 | Lim | 435/178 |
| 4,353,888 | 10/1982 | Sefton | 424/424 |
| 4,647,536 | 3/1987 | Mosbach et al. | 435/177 |
| 4,673,566 | 6/1987 | Goosen et al. | 424/424 |
| 5,116,747 | 5/1992 | Moo-Young et al. | 435/178 |

*Primary Examiner*—Richard D. Lovering
*Attorney, Agent, or Firm*—Flehr, Hohbach, Test, Albritton & Herbert

[57] ABSTRACT

A method for encapsulating a biological substance is biocompatible microcapsules is disclosed, said method comprising:

a) maintaining a coating-forming liquid film sheet comprising a solution of a soluble organic polymer in an organic solvent, b) causing droplets comprising biological substance is an aqueous medium to pass through said sheet to form microcapsules comprising cores of said droplets coated by said liquid film, and c) permitting said microcapsules to pass through said sheet so that a portion of said polymer precipitates in the presence of water in said droplets while evaporating a portion of said solvent to form a continuous permeable polymer coating of sufficient structural that said microcapsules are self-supporting.

10 Claims, 1 Drawing Sheet

METHOD OF ENCAPSULATING BIOLOGICAL SUBSTANCES IN MICROSPHERES

BACKGROUND OF THE INVENTION

Many clinical conditions, deficiencies, and disease states can be remedied or alleviated by supplying to the patient a factor or factors produced by living cells or removing from the patient deleterious factors which are metabolized by living cells. In many cases, these factors can restore or compensate for the impairment or loss of organ or tissue function. Examples of disease or deficiency states whose etiologies include loss of secretory organ or tissue function include (a) diabetes, wherein the production of insulin by pancreatic islets of Langerhans is impaired or lost; (b) hypoparathyroidism, wherein the loss of production of parathyroid hormone causes serum calcium levels to drop, resulting in severe muscular tetany; (c) Parkinsonism, wherein dopamine production is diminished; and (d) anemia, which is characterized by the loss of production of red blood cells secondary to a deficiency in erythropoietin. The impairment or loss of organ or tissue function may result in the loss of additional metabolic functions. For example, in fulminant hepatic failure, liver tissue is rendered incapable of removing toxins, excreting the products of cell metabolism, and secreting essential products, such as albumin and Factor VIII. Bontempo, F. A., et al., Blood 69:1721 (1987).

In other cases, these factors are biological response modifiers, such as lymphokines or cytokines, which enhance the patient's immune system or act as anti-inflammatory agents. These can be particularly useful in individuals with a chronic parasitic or infectious disease, and may also be useful for the treatment of certain cancers. It may also be desirable to supply trophic factors to a patient, such as nerve growth factor or insulin-like growth factor-one or -two (IGF1 or IGF2).

In many disease or deficiency states, the affected organ or tissue is one which normally functions in a manner responsive to fluctuations in the levels of specific metabolites, thereby maintaining homeostasis. For example, the parathyroid gland normally modulates production of parathyroid hormone (PTH) in response to fluctuations in serum calcium. Similarly, β cells in the pancreatic islets of Langerhans normally modulate production of insulin in response to fluctuations in serum glucose. Traditional therapeutic approaches to the treatment of such diseases cannot compensate for the responsiveness of the normal tissue to these fluctuations. For example, an accepted treatment for diabetes includes daily injections of insulin. This regimen cannot compensate for the rapid, transient fluctuations in serum glucose levels produced by, for example, strenuous exercise. Failure to provide such compensation may lead to complications of the disease state; this is particularly true in diabetes. Jarret, R. J. and Keen J., Lancet (2):1009 (1976).

Accordingly, many investigators have attempted to reconstitute organ or tissue function by transplanting whole organs, organ tissue, or cells which provide secreted products or affect metabolic functions. Moreover, transplantation can provide dramatic benefits but is limited in its application by the relatively small number of organs suitable and available for grafting. In general, the patient must be immunosuppressed in order to avert immunological rejection of the transplant, which results in loss of transplant function and eventual necrosis of the transplanted tissue or cells. In many cases, the transplant must remain functional for a long period of time, even for the remainder of the patient's lifetime. It is both undesirable and expensive to maintain a patient in an immunosuppressed state for a substantial period of time.

A desirable alternative to such transplantation procedures is the implantation of cells or tissues within a physical barrier which will allow diffusion of nutrients, waste materials and secreted products, but block the cellular and molecular effectors of immunological rejection. A variety of devices which protect tissues or cells producing a selected product from the immune system have been explored. These include extravascular diffusion chambers, intravascular diffusion chambers, and implantation of microencapsulated cells. Scharp, D. W., et al. World J. Surg. 8:221 (1984). These devices were envisioned as providing a significant advance in the field of transplantation, as they would alleviate the need to maintain the patient in an immunosuppressed state, and would thereby allow many more patients to receive restorative or otherwise beneficial transplants by allowing the use of donor cells or tissue which could not have been used with the conventional transplantation techniques. However, none of these approaches have been satisfactory for providing long-term transplant function. A method of delivering appropriate quantities of needed substances, such as enzymes and hormones, or of providing other needed mebaolic functions, for an extended period of time is still unavailable and would be very advantageous to those in need of long-term treatment.

A number of different techniques have been used for microencapsulation of living cells. For example, live mammalian cells have been microencapsulated in calcium alginate gels and then coated with polylysine and/or polyethylene imine. O'Shea, G. M., et al., Biochim. Biophys. Acta., 804:133 (1984).

In prior microcapsules, cells in the core of the microcapsule where linked to the jacket or coating by ionic bonds between oppositely charged polymers. See e.g., Raj, U.S. Pat. No. 4,744,933 and Lim and Sun, U.S. Pat. Nos. 4,352,833 and 4,409,331.

The use of water insoluble, hydrophilic polyacrylates has been disclosed for the microencapsulation of mammalian cells. Sefton, M. W., et al., Biochim. Biophys. Acta., 717:473 (1982). Further modification of this technique includes encapsulation of such cells in a water insoluble polyacrylate by co-axial extrusion and interface precipitation. Sugamori, M. E., et al., Trans. Am. Soc. Atrif. Intern. Organs, 35:791 (1989). The system discloses an inner and outer barrel with the cells flowing through the inner barrel and polymer through outer barrel. Polymer-coated droplets formed at the tip of the extruder are forced off by a co-axial airstream and fall into a precipitation bath. There, microcapsules are formed having cores of the living cells within a polymer coating.

SUMMARY OF THE INVENTION

The invention relates to a method for forming biocompatible microcapsules. Droplets of biological substances such as living cells in aqueous medium pass through a coating-forming liquid film sheet to form microcapsules in which the droplet cores are coated by the liquid film. In one embodiment, the sheet is a solution of a soluble polymer dissolved in an organic solvent. After passing through the liquid film sheet, the polymer precipitates in the presence of water within the droplets while driving the solvent away from the droplet to form a self-supporting continuous polymer coating for the microcapsule. The sheet is preferably disposed transverse to a vertical plane to permit the microcapsules to fall under the influence of gravity. Alternatively, the sheet may be vertical.

In another embodiment, the coating-forming liquid film comprises a polymerizable monomer liquid. The liquid film coatings on the microcapsules are polymerized after passing through the film to form a self-supporting permeable polymer coating.

DESCRIPTION OF PREFERRED EMBODIMENTS

Figure 1:
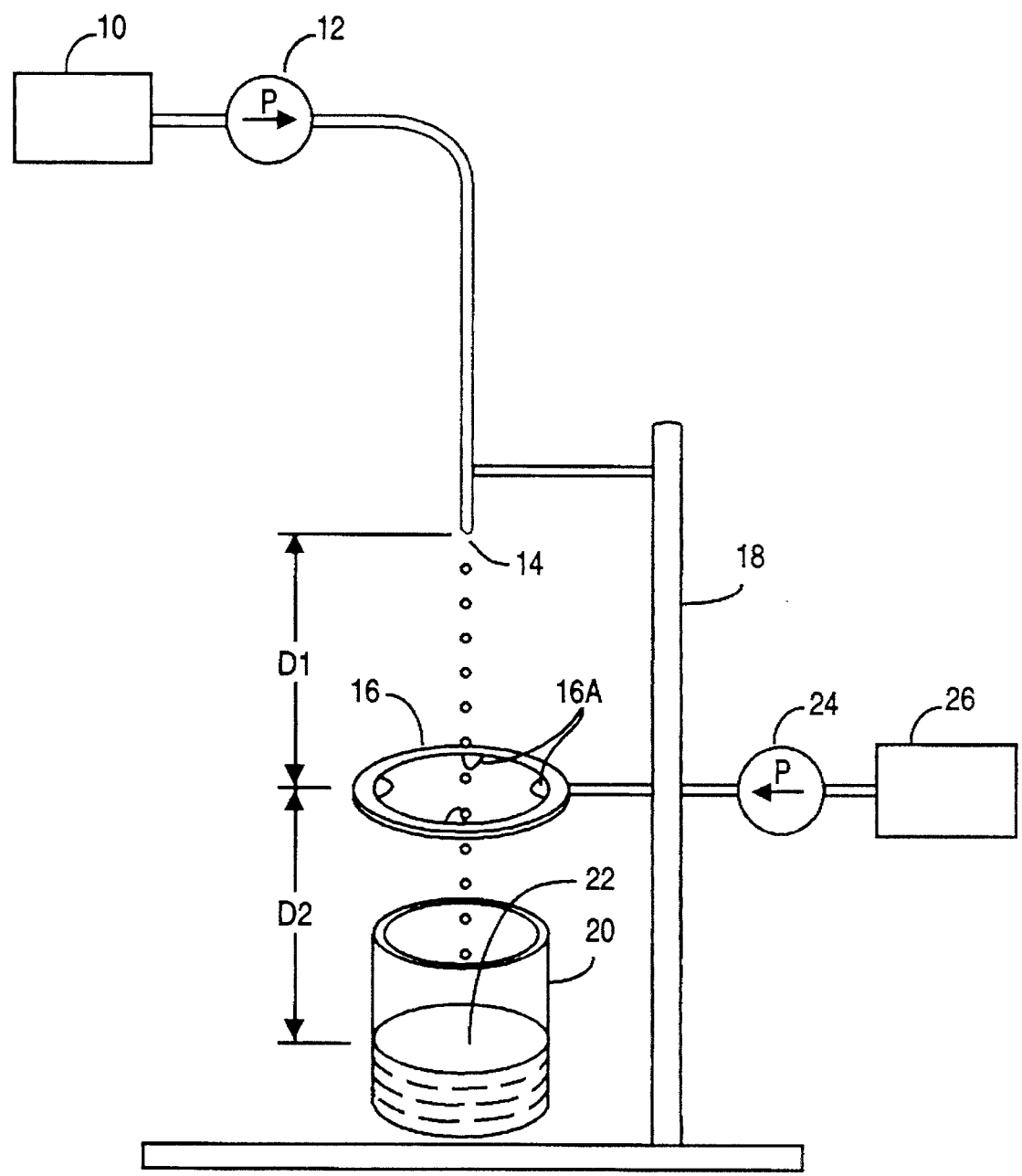
FIG. 1 is a schematic representation of an apparatus for performing the method of the present invention.

The present invention relates a method for encapsulation of biological substances in biocompatible microspheres which can be implanted into an individual, i.e., a human or animal subject. The biological substances which are encapsulated can include cells capable of secreting a selected biologically active product or providing a selected biological function to the individual. Alternatively, the biological substances could comprise treatment agents, e.g., growth factors, tropic factors, or neurotransmitters for slow release into the body.

The term microcapsule is well-recognized in the field to include a core of biological substances in an aqueous medium surrounded by a permselective membrane. The core could include such materials in a matrix such as a hydrogel, e.g., as disclosed in omnibus patent application, Ser. No. PCT/US92/03327.

The core may include cells in any form, including but not limited to, cells retained in tissue, cell cultures, and individually isolated cells.

The term microcapsule as defined herein includes generally spherical capsules with an outer permselective coating and a core of biologically active substances as described above. The shape of the microcapsules is determined by the shape of the droplets. Although such droplets are generally spherical in shape, the shape may vary considerably from the spherical depending on the encapsulation conditions. Such capsules may have a broad size range, typically from about 0.2 to 2 mm nominal diameter. Nominal diameter refers to the approximation of the maximum linear dimension corresponding to a diameter for a microcapsule which is not totally spherical, i.e., having somewhat irregular shaped outer wall.

The microcapsules are permselective to allow passage of molecules of the desired size. For example, assuming the substances are living cells producing a biologically active substance to be secreted into the individual, the walls of the microcapsules are sufficiently permeable to permit passage of the substance but to retain the cells and prevent the passage of substances from the individual's system into the microcapsules which could be detrimental to the viability of the cells. A suitable permeability of the cells is that which permits passage of molecules of 100 Daltons to 500 kD.

The jacket of the microcapsule is also biocompatible. That means that it does not elicit a detrimental host response sufficient to result in rejection of the implanted vehicle or to render it inoperable. The jacket material should also avoid unfavorable tissue responses such as fibrosis.

In one embodiment of the present invention, the biocompatible microcapsules are formed in the following manner.

In step (a), a coating-forming liquid sheet is maintained. Preferably, the sheet is transverse to a vertical plane. More preferably, it is maintained in a generally horizontal plane to facilitate intersection of falling droplets. The liquid film sheet is preferably maintained in surface tension contact with a solid boundary surface, suitably in the form of a ring or other shape defining an open interior. The solution may be continuously fed to the boundary as through multiple inwardly directed ports on the ring. In an embodiment not shown, the sheet may even be disposed in a generally vertical plane if the droplets are propelled against the sheet from one side to pass through on the other side of the sheet.

The coating-forming liquid may comprises a solution of a soluble organic polymer dissolved in an organic solvent. The proportion of the polymer to solvent is selected so that the liquid film remains in a continuous sheet during falling of the droplets and so that sufficient solution coat the droplets on passage through the liquid film to form a continuous coating or jacket. Such proportions depend upon the specific solution. In general, suitable proportions are from about 10 to 20% on a weight:volume basis and preferably about 10 to 15%.

In step (b), biological substance droplets are caused to fall downwardly through the liquid film sheet to form microcapsules comprising cores of the droplets coated by the liquid film. As discussed above, the droplets are in an aqueous medium and can include living cells or other biological substances. The cells may be presuspended in an aqueous culture medium, or suspended in a matrix, such as alginate or chitosan, or supported on a solid carrier such as a preformed gelatin bead. In addition, a plurality of cell containing microcarriers may be encapsulated. Suitable microcarriers are the commercially available ones used in bioreactors such as Cytodex beads, commercially available from Sigma Chemical Company.

The droplets are caused to fall either by gravity or by propulsion at a controlled rate from a pump above the sheet. The speed of the gravitating droplets is sufficient to pass through the liquid film sheet and to deposit a coating of the polymer solution on passage through the sheet to form the microcapsules.

In step (c), after passing through the wet liquid film sheet, the microcapsules are permitted to fall downwardly to cause a portion of the organic polymer to precipitate in the presence of the water in the droplets while evaporating solvent to form a continuous polymer coating of sufficient structural integrity so that the microcapsules are self-supporting. The surface tension viscosity of the polymer film causes the formation of the outer layer on the biological material in a manner analogous to the formation of bubbles.

The formation of the continuous polymer coating is a phase inversion phenomenon. The polymer/solvent system is chosen so that after precipitation or coagulation of the polymer in a continuous coating around the cells the polymer precipitates in the aqueous medium of the biological substance. Precipitation occurs as the polymer contacts the interface between the solvent and the aqueous medium in which it has been soluble. The polymer/solvent system is chosen so that precipitation of the polymer occurs to form a complete self-supporting coating prior to contact of the capsule with a collection of basin. The polymer should be sufficiently soluble in the solvent to avoid rapid precipitation which could lead to incomplete encapsulation. On the other hand, the polymer/solvent system is to those sufficient intrinsic viscosity to form a relatively stable film. A suitable viscosity for the film is from about 250 to 900 cps. Preferable thicknesses for the coatings on the droplets range from about 5 microns to 50 microns provide the desired structural strength and viscosity.

The solvent will depend upon the specific chosen polymer. Suitable solvents are organic and water miscible. Such solvents include dimethylsulfoxide, dimethylformamide, and dimethylacetamide.

Suitable polymers include thermoplastic polymers such as polyacrylonitrile (PAN), polyvinylchloride (PVC), polysulfone, poly (ether sulfone) cellulose acetate, and the like. Polymers should be chosen such that they are capable of forming a self-supporting film in solution and are biocompatible.

Alternatively, the polymer may be a biocompatible elastomer, such as polyurethane. Suitable polyurethanes include products sold under the trademarks Cardiothane and Biomer. The advantages of elastomers is that elastomeric microcapsules may be cryo-preserved and do not tend to crack with the expansion and contraction caused by freezing and thawing.

After step (c), the microcapsules are collected in a manner to minimize deformation. In one embodiment, the microcapsules fall into a liquid bath in a basin. A suitable bath includes physiological buffer solutions which serve to dilute the organic solvent. Alternatively, the microcapsules can be collected on a soft surface such as one formed of foam rubber.

In another embodiment of the invention, the coating-forming liquid film sheet comprises an organic polymerizable monomer liquid. The monomer liquid may be in a solvent or not. It is formed into the liquid film sheet of the same physical characteristics as the polymer/solvent solution. The microspheres are coated by the monomer on falling through the liquid film sheet. The liquid film coating is thereafter subjected to polymerization conditions during continuing descent of particles to form a permeable polymer coating of sufficient structural integrity so that the microcapsules are self-supporting.

In this embodiment, biocompatible monomers are subjected to suitable polymerization conditions such as photopolymerization radiation to complete and formation of the film prior to contact with the collection piece. In one system the monomer is polyethylene glycol (PEG), α- and ω-terminated with hydroxyl moieties and activated with acrylyl chloride α-, ω-diacrylyl PEG (PEG-DA). Such compounds are photocurable. (Sawhney, A. S., et al. *Fourth World Biomaterials Congress*, Apr. 24–28, 1992 (Berlin, Germany)).

Referring to FIG. 1, a suitable apparatus is illustrated for performing the method of the present invention. A solution containing the cell medium is contained in the storage vessel 10 and is pumped by pump 12 to a nozzle 14 which forms droplets which gravitate a distance D1 to means for retaining the liquid film sheet in a generally horizontal direction. Suitable means comprises a wire loop 16 retained by stand 18. At a distance D2 below loop 18 is a collection vessel 20 which includes a collection bath 22. An advantage of the collection bath is that it provide a soft landing for the microcapsules to minimize deformation of the outer coating and possible rupture. Alternatively, another soft landing area may be provided as with foam rubber or like.

The nozzle 14 of the biological substance feed material is located at a distance D1 from the plane of the loop. It may be adjusted to allow sufficient velocity to the falling droplets under the influence of gravity to permit complete encapsulation for a typical polymerization system. If desired for a particular system, the biological materials may be mechanically accelerated using, for example, an actuated mechanical piston system, such as a syringe pump to force droplets through an orifice.

The liquid film sheet may be filled into loop 16 in a batch or continuous manner. Referring to the former, the loop may be dipped into a reservoir of the polymer solution and retracted with the sheet in place under the influence of surface tension effects similar to drawing a film in a loop for blowing bubbles. The loop may be of an appropriate size to permit the sheet to form. Typically loop sizes provide sheets on the order of 1 to 10 $cm^2$ surface area. Larger surfaces may also be used to support sufficient polymer solution so that multiplicity of microcapsules may be prepared subsequent to a single dip.

A continuous feed system is illustrated in FIG. 1. There, a pump 24 feeds the polymer solution from source 26 to loop 16 by multiple spaced-apart inwardly and directed nozzles 16*a*. In this instance, the loop is hollow with internal perforations through which the polymer solution is fed to form the liquid film sheet. It is retained in place by surface tension.

Collection bath 22 comprises a biocompatible aqueous medium, such as an aqueous sterile phosphate buffered saline solution. Alternatively, the bath may have a layer of an inorganic phase above the aqueous phase, e.g., of the type illustrated and discussed in U.S. Pat. No. 4,353,888. If desired, the collection bath may be stirred.

As described above, suitable distances for D2 between the liquid film and collection bases for permitting adequate polymerization using a polymer/solvent system are to be optimized depending upon the characteristics of the polymer and solvent.

The following examples illustrate to both systems for performing the method of the present invention.

EXAMPLE 1

PC12 Cells

The following system uses the general system of FIG. 1.

PC12 cells were cultured in standard RPMI. The cells were taken up by pipette, placed in centrifuge tubes and spun down. The cells were brought up to a volume of 2 ml, to a cell concentration of approximately $2\times10^6$ to $5\times10^6$ per ml. The cell containing liquid was placed in sterile Hamilton syringe and placed on a Harvard apparatus injector pump. The pump was connected via 18 gauge polytetrafluoroethylene tubing to a 24 gauge stainless steel tube, which served as an apparatus for dropping the liquid.

A 0.42 mm stainless steel wire configured into a 14 mm hoop was used to support a polymer film. The polymer system was 12% PAN in DMF (w/v). The film was prepared by drawing the hoop into a container of polymer and drawing off the excess liquid. The hoop was positioned in the droplet path 33 cm below the aperture and 15.5 cm above the surface of the collection bath. A 2,000 ml breaker containing 1,000 ml sterile PBS served as the collection bath.

Microcapsules were formed by pumping droplets through the aperture and allowing the drops to pass through the film into the bath.

Approximately 12 microcapsules were sampled about 5 minutes after encapsulation and were tested with FDA and all microcapsules showed green fluorescence, a positive test for living cells. Microscopic examination showed viable cells existing in small aggregates of approximately 5–20 cells.

A sample of the microcapsules was placed in culture and held for four weeks. At the end of six weeks, the microcapsules showed viable cells.

Microcapsules were examined by SEM and showed coating thicknesses of 15–35 microns.

EXAMPLE 2

BAC cells in alginate

Microcapsules containing bovine adrenal chromaffin cells in a 1.5% sodium alginate solution (W/V) were prepared according to Example 1. The PBS collection bath container contained 1.5% (W/V) calcium chloride. After six weeks in culture, the microcapsules contained viable cells.

Polymer/solvent systems which have been used to form successful microcapsules according to the present invention are set forth in the following Table 1.

TABLE OF SYSTEMS WHICH WORK
Polymer/Solvent Systems for Forming Microcapsules

| Polymer | Solvent | Conc. (W/V) |
| --- | --- | --- |
| Polyacrylonitrile | DMSO<br>DMF<br>DMAC | 12–15% |
| Cellulose acetate | DMAC | 12–16% |
| PAN-PVC | DMF<br>DMAC | 12–16% |
| Polyurethane | DMF | 10–16% |
| Polyurethane/<br>Polyethylene<br>oxide copolymer | DMAC | 10–16% |

What is claimed is:

1. A method for encapsulating a biological substance in biocompatible microcapsules comprising:
   (a) maintaining a coating-forming liquid film sheet, said sheet comprising a solution comprising a soluble organic polymer dissolved in an organic solvent,
   (b) causing droplets comprising biological substances in an aqueous medium to pass through said sheet to form microcapsules comprising cores of said droplets coated by said liquid film, and
   (c) permitting said microcapsules to pass through said sheet so that a portion of said polymer precipitates in the presence of the water in said droplets while evaporating a portion of said solvent to form a continuous permeable polymer coating of sufficient structural integrity so that said microcapsules are self-supporting.

2. The method of claim 1 in which said sheet is disposed transverse to a vertical plane and said droplets pass downwardly through said sheet.

3. The method of claim 1 in which said biological substance comprises cells capable of secreting a selected biologically active product or of providing a selected biological function to an individual.

4. The method of claim 1 in which said sheet is maintained by surface tension contact with a solid boundary surface.

5. The method of claim 4 in which said solution is continuously fed to said boundary surface.

6. The method of claim 1 in which said polymer is a thermoplastic polymer.

7. The method of claim 6 in which said thermoplastic polymer is selected from the group consisting of polyacrylonitrile, polyvinyl chloride, polysulfone, cellulose acetate, and mixtures thereof.

8. The method of claim 1 in which the ratio of said polymer to said solvent in said sheet comprises from about 10% to 20%:1 on a weight:volume basis.

9. The method of claim 1 in which said polymer is an elastomeric polymer.

10. The method of claim 9 in which said elastomeric polymer comprises polyurethane.

* * * * *